US006194720B1

(12) United States Patent
Li et al.

(10) Patent No.: US 6,194,720 B1
(45) Date of Patent: Feb. 27, 2001

(54) PREPARATION OF TRANSMISSION ELECTRON MICROSCOPE SAMPLES

(75) Inventors: Du Li, Meridian, ID (US); Rose Zou, Mountain View, CA (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 09/105,128

(22) Filed: Jun. 24, 1998

(51) Int. Cl.[7] .............................. G01N 1/28; G01N 1/32; H01J 37/20
(52) U.S. Cl. ......................... 250/311; 250/306; 438/690; 438/691; 438/455; 438/460
(58) Field of Search .................................. 250/311, 306, 250/307; 438/690, 691, 455, 460, 14, 22

(56) References Cited

U.S. PATENT DOCUMENTS

| 5,656,811 | * | 8/1997 | Itoh et al. | 250/309 |
| 5,940,678 | * | 8/1999 | Doong et al. | 438/14 |
| 5,990,478 | * | 11/1999 | Liu | 250/307 |

OTHER PUBLICATIONS

J. Benedict, R. Anderson, S.J. Klepeis, "Recent Developments in the use of the tripod polisher for TEM speciment preparation", Mat. Res. Soc. Symp. Proc. vol. 254, 1992, pp121–142. .

FEI Company, "Pre–FIB TEM Sample Preparation", PN 19864 Rev A, Mar. 4, 1997, pp. 1–17.

FEI Company, "FIB TEM Sample Preparation", PN 19575 Rev B, Mar. 4, 1997, pp. 1–30.

* cited by examiner

*Primary Examiner*—Bruce C. Anderson
*Assistant Examiner*—Nikita Wells
(74) *Attorney, Agent, or Firm*—Knobbe Martens Olson & Bear, LLP.

(57) ABSTRACT

A sectional transmission electron microscope (TEM) specimen and a method of forming the same is provided. The specimen includes two separate electron transparent regions, namely a first electron transparent segment for analyzing a specific feature and a second electron transparent segment for analyzing bulk features. The first electron transparent segment is formed using a focused ion beam (FIB) technique, while the second electron transparent segment is formed by a wedge forming technique. The latter step is carried out by protecting the first segment with an adhesive filler and a covering glass layer, polishing a surface of the specimen at an angle to an opposite surface, while simultaneously exposing the previously formed first segment, and removing the filler and glass layer.

30 Claims, 5 Drawing Sheets

PREPARATION OF TRANSMISSION ELECTRON MICROSCOPE SAMPLES

BACKGROUND OF THE INVENTION

1. Field of the Invention

The present invention relates to the field of specimen preparation and more particularly to the preparation of thin specimens for use in transmission electron microscopy.

2. Description of the Related Art

Transmission electron microscopy (TEM) is one of the most important techniques available for the detailed examination and analysis of the micro-structural characteristics of many materials. The TEM technique provides high resolution imaging, sensitive chemical spectroscopy and material analysis of thin specimens with thicknesses in the range of 0.01–0.2 $\mu$m. The successful use of TEM in direct observation of fine microstructural features has made the TEM technique a necessary analytical tool in semiconductor circuit fabrication. In the semiconductor industry, the TEM technique is generally used for characterizing the materials to be used in semiconductor circuits and for examining the actual structures fabricated from these materials. It cannot be overemphasized that good specimen preparation is the most important requirement of the transmission electron microscopy technique.

The specimens required for transmission electron microscopy should be very thin to make the specimen transparent to electrons. The prepared specimen should also be representative of that found in the bulk material. In other words the microstructure should be unaltered by the preparation procedure. Particularly, in ultra large scale integrated circuit (ULSI) technologies, cross-sectional TEM specimens are especially important.

In (ULSI) designs, the control of ULSI device parameters requires a detailed knowledge of the cross-sectional geometry of individual devices. This can be provided by the cross-sectional specimens which enable direct imaging to be made of the vertical structure of epitaxial layers, ion implanted layers or device structures in ULSI technologies. A typical cross-sectional specimen preparation involves initially identifying a specific feature to be used for the TEM analysis, such as a particular device in an array of memory cells. After the specific feature has been identified, the wafer is cleaved or sawed to produce a rectangular specimen with this particular device of interest located at the center of this specimen. In the next step, the specimen can be reduced to a rectangle by sawing, grinding and polishing. In general, this final size is defined by the size of the specimen housing of the TEM specimen holder, which generally cannot receive specimens larger than approximately 3 mm in diameter. Following this, the specimen is further thinned down to the electron transparency thickness.

There are various techniques for producing electron transparent specimens for cross-sectional transmission electron microscopy studies. Some of these techniques produce a thin electron transparent region having a wedge profile and thus these techniques may be referred to as wedge forming techniques. One well-known wedge forming technique is ion beam milling. In the ion beam milling technique, the specimen is first glued on a specimen grid and then loaded on a holder and placed in the path of one or more ion beams. The specimen grid is a hollow metallic disk for supporting the specimen during ion milling and the TEM examination. The ion beams, angled with respect to the specimen, gradually remove atoms from the surface of the specimen until a small perforation is formed in the center of the specimen. Due to the gradual thinning occurring towards the perforation, a narrow band of material around the perforation forms a wedge profile which is thin enough to allow high energy electrons to pass through. Although ion milling offers a cross-section with a large wedge, this process takes a very long time to reduce specimen thickness down to the electron transparent range. Additionally, it is difficult to prepare specimens with this process quickly and on a reproducible basis to meet the growing needs of the semiconductor industry for TEM analysis.

Tripod polishers can also be used to mechanically thin the specimens to electron transparency thickness ranges. As is well known in the art of TEM specimen preparation, a tripod polisher is a device for holding specimens on a rotating abrasive medium for the mechanical thinning of the specimens. While the process, a specimen is mounted on the tripod polisher and mechanically polished on one side using a sequence of progressively finer polishing films. When the desired feature is reached on one side, the specimen is flipped over on the tripod polisher and polished from the other side, using the same sequence of polishing films to reach the predefined feature of interest. During the polishing on the second side, the tripod polisher is set at a slight angle to produce a tapered or wedge shaped specimen, with the feature of interest at the thin edge of the specimen. This thin edge is electron transparent, typically having a thickness of approximately 0.1 micron across a typical width of approximately 0.5–1.0 mm. The polishing thus eliminates the need for ion milling or reduces ion milling process time to few minutes. However, specific features can easily be damaged in the tripod polishing process. Furthermore, it is difficult to locate specific features, particularly features with submicron dimensions, using wedge forming techniques.

An alternative to wedge forming techniques is the focused ion beam (FIB) process. A specimen having the feature of interest is initially ground to approximately 50 $\mu$m thickness, this thickness being measured transverse to the wafer surface. Commonly, the specimen is dimensioned to have approximately a height of about 0.6 mm (the thickness of the Si wafer) and a 2 mm width, in order to fit on a 3 mm diameter TEM grid. Typically, the feature of interest is half way through the 50 $\mu$m thickness of the specimen. A slotted TEM grid is used to support the specimen during the FIB process. However, a quadrant of the supporting grid needs to be cut away to permit access of the ion beam to the specimen surface during the FIB process. The specimen is then centered and glued on a slotted grid with the cross-section of the specimen (the 0.6 mm×2 mm surface) onto the grid surface. The wafer surface of the specimen is aligned to face the opening of the grid when it is glued. The grid carrying the specimen is mounted on a FIB sample holder and inserted into a FIB work station. The specimen holder positions the specimen in the correct orientation to allow an ion beam access normal to the specimen surface (originally the wafer surface) where the specific feature is located. The ion beam mills both sides of the feature. The focused ion milling forms a very thin and uniform membrane between two trenches dug by the ion beams. The finished specimen is transferred to the TEM system for imaging and analysis.

However, this FIB milling procedure has several shortcomings, which have thus far limited its application in the TEM specimen preparation field. One problem of this procedure is that the available area for TEM analysis is limited by the size of the membrane, so that only a specific location can be examined. Additionally, trench walls present a particular problem for the TEM x-ray compositional analysis (EDSanalysis), since these walls block the path of x-rays generated in the membrane region. Another problem is associated with the use of the slotted grid on which the specimen is mounted. If the grid is distorted during cutting, the alignment of the specimen surface to the beam becomes very difficult.

Accordingly, a need exists for more reliable specimen preparation techniques. Desirably, such specimen preparation techniques should be compatible with the current semiconductor device fabrication technologies and performance.

SUMMARY OF THE INVENTION

The aforementioned needs are satisfied by several aspects of the present invention.

In accordance with one aspect of the present invention, a cross-sectional electron microscope specimen is provided. The specimen includes a first electron transparent segment of the substrate to be analyzed. The specimen also includes a second, separate electron transparent segment on the same substrate.

In particular, in accordance with the preferred embodiment, the first electron transparent segment is a thin membrane formed by a focused ion beam process, whereas the second electron transparent segment is a tapered corner of the substrate, formed by polishing two opposite sides of the substrate at angles to one another. Advantageously, a specific feature of interest (e.g., a single memory cell in a DRAM array) is positioned in the first segment for cross-sectional analysis, while the second substrate may be representative of the bulk substrate. Preparing both samples in a single specimen, of course, presents significant time and cost savings.

In accordance with another aspect of the present invention, a cross-sectional transmission electron microscope specimen is provided. The specimen includes a first electron transparent segment which is recessed within a substrate die. The specimen additionally includes a second electron transparent segment having a tapered thickness. In accordance with an exemplary embodiment, the first segment is doubly recessed from upper and lower surfaces of the specimen. In the exemplary embodiment, the surfaces are polished to form a tapered thickness for the second segment while at the same time reducing the amount by which the first segment is recessed from those surfaces. X-rays are thus not blocked by steep side walls for such a shallow recess, and EDS analysis can be conducted on the first segment.

In accordance with another embodiment of the present invention, a specimen is provided for material analysis. In particular, the specimen is a partially or fully fabricated integrated circuit on a semiconductor substrate. The specimen includes a first segment positioned within a trench, which extends between first and second surfaces of the specimen. This first segment is oriented parallel to one of the first and second surfaces, and includes a fabricated feature of integrated circuit. The specimen additionally includes a second segment formed at a tapered edge of the specimen. The second segment includes bulk material of the semiconductor substrate and the general feature of the fabricated integrated circuit on the semiconductor substrate.

In accordance with another aspect of the present invention, a process is provided for preparing a transmission electron microscope specimen. The process includes forming a first segment in the specimen, where the first segment has upper and lower surfaces separated by an electron transparent thickness. After this first segment is formed, an upper portion of the specimen is removed to expose the upper surface of the segment.

In accordance with another aspect of the present invention, a method is provided for forming a specimen of a substrate for material analysis of two distinct segments. The method includes milling a trench on the surface of the substrate on either side of a feature of interest, thus forming a membrane which extends generally perpendicular to the milled surface. A first portion of the substrate is removed to form a first finished specimen surface, which is generally parallel to the membrane. Removing the first portion additionally exposes a first surface of the membrane. A second portion of the substrate is removed at an angle to the first finished specimen surface, forming a second finished specimen surface and additionally exposing a second surface of the membrane.

In accordance with another aspect of the present invention, a method is provided for preparing a specimen for cross-sectional analysis. The method includes focused ion beam milling to form a first trench on a first side of the feature to be analyzed. A second trench is formed on a second side of the feature of interest, also by focused ion beam milling. Side walls of the trenches are then removed by polishing the die.

In accordance with another aspect of the present invention, a process for preparing a TEM specimen includes providing an electron transparent segment within a substrate. The segment is protected with a removable filler layer and a protective cover layer. Portions of the substrate and the filler layer are removed to reduce the substrate to a desired thickness.

BRIEF DESCRIPTION OF THE DRAWINGS

These and several other aspects of the invention will be apparent to one of skill in the art from the following description, and from the drawings in which.

DETAILED DESCRIPTION OF THE PREFERRED EMBODIMENT

Reference will now be made to the drawings wherein like numerals refer to like parts throughout. As will be described hereinbelow, a preferred embodiment of the present invention provides a process for preparing a cross-sectional transmission electron microscope (TEM) specimen with a first electron transparent segment for analyzing a specific feature, and a second electron transparent segment having bulk features. In the illustrated embodiment, the first electron transparent segment is formed using a focused ion beam milling technique while the second electron transparent segment is formed by a wedge forming technique.

Figure 1:
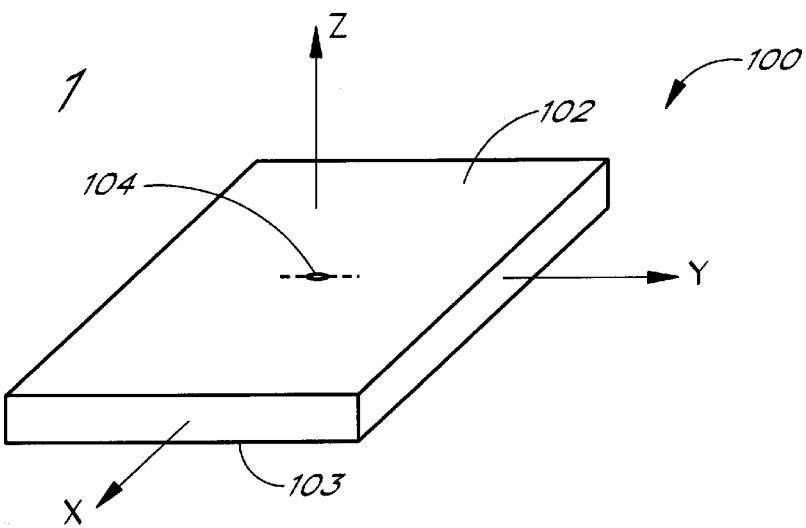
FIG. 1 is a perspective view of a substrate used to prepare a transmission electron microscope (TEM) specimen.

In accordance with the preferred embodiment, the process is initiated with the preparation of the first electron transparent area of the TEM specimen. FIG. 1 illustrates a die 100 that is sliced out from a substrate, such as a semiconductor wafer including deposited layers and doped areas, for the purpose of cross-sectional transmission electron microscope specimen preparation. The die 100 preferably comprises a ULSI-die, having an upper surface 102 and a lower or bottom surface 103. For purposes of illustration, an xyz coordinate system is shown in FIG. 1. In this coordinate system, the upper surface 102 is parallel to an x-y plane defined by the x- and y-axes. A z-axis extends perpendicular to the upper surface 102. An exemplary die has a length along the x-axis of about 3–5 mm, a width along the y-axis of about 8–10 mm, and thickness in the z dimension of about 0.5 mm.

The ULSI-die 100 preferably includes a specific feature 104 to be studied in a transmission electron microscope (TEM). The feature 104 may, for example, be a failing semiconductor device such as a capacitor made of a number of sequentially deposited layers, or a metal contact in a memory cell. In the semiconductor industry, such failing devices are commonly located through electrical-failure-site maps using various surface and voltage features. Such a feature 104 would have a microstructure penetrating into the bulk of the ULSI die 100 and may be surrounded by other microstructures such as other cell circuitry. For purposes of illustration, the feature 104 of interest will be assumed to be in a y-z plane defined by the z and y axes. It will be appreciated that since the feature 104 is included in the y-z plane, the y-z plane defines a cross-section plane of the specimen 100 to be exposed in specimen preparation.

In other arrangements, the feature of interest can be an emitter tip formed in a substrate. As disclosed, for example, in U.S. Pat. No. 5,229,331, issued to Doan et al. on Jul. 20, 1993, such emitter tips are typically used to emit electrons, which then impinge upon phosphor upon a screen to light a pixel. The disclosure of U.S. Pat. No. 5,229,331 is hereby expressly incorporated by reference. The tip comprises a sharp cone feature which may be formed by oxidation, selective etching, or patterned etching, as will be understood by one of ordinary skill in the art.

After identifying the feature 104 of interest on the die surface 102, the first electron transparent segment may be formed using a first material thinning technique. In the preferred embodiment, the first material thinning technique comprises a focused ion beam milling technique. In the focused ion beam ("FIB") technique, the die 100 is mounted on a specimen holder (not shown) and conveniently placed into a focused ion beam chamber (not shown) for focused ion beam milling. Advantageously, a relatively large die sitting flatly on the FIB specimen holder makes it easy to align the specimen to the ion beam, and hence, the FIB time for TEM specimen preparation is reduced.

Figure 2A:
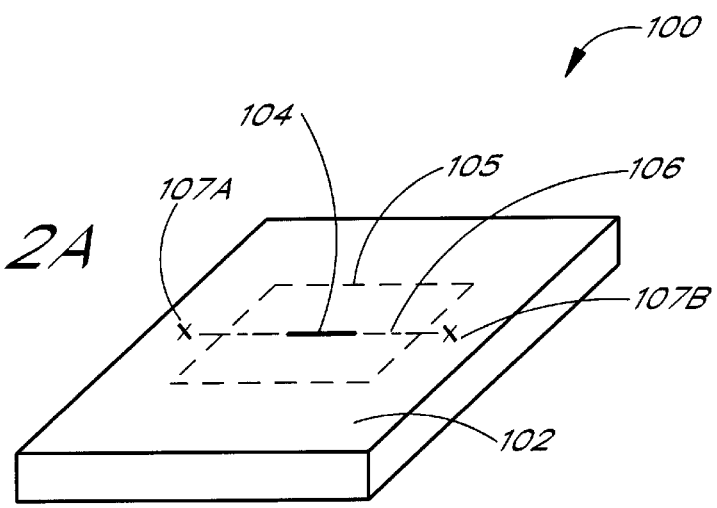
FIG. 2A is a perspective view of the substrate shown in FIG. 1 wherein an observation area and a cross-section reference line are defined on the substrate, in accordance with a first embodiment of present invention.

Preparation of the first electron transparent segment on the die 100 will now be described in detail, with reference to FIGS. 2A through 2D. As illustrated in FIG. 2A, an observation area 105, which includes the feature 104 to be observed in cross-section, is determined and marked on die 100 by an imaging system (not shown) of the FIB system. The observation area 105 may have a rectangular shape and is often referred to in the art as a reference box. The box 105 is preferably aligned such that the feature 104 is positioned at the center of the box 105.

Referring to FIG. 2A, with the feature 104 at the center of the box, the desired cross-sectional plane is identified by marking a cross-section reference line 106 between reference marks 107A and 107B. The reference marks 107A and 107B are etch spots created by the focused ion beam outside the box 105.

Once the position of the feature 104 and the cross-sectional plane is determined, the feature may be covered with a protective film (not shown). Such protective films are well known in the FIB process and often used to protect the feature from over etch and from being damaged during the FIB process. In the preferred embodiment, the protective film comprises a bilayer including a layer of silicon dioxide ($SiO_2$) and a layer of platinum metal. A $SiO_2$ film is initially deposited on the feature. A preferred thickness for the $SiO_2$ film is in the range of about 0.1–0.2 $\mu$m. Following $SiO_2$ deposition, a layer of platinum is deposited on the $SiO_2$ film. The platinum film can have a thickness in the range of about 0.3–0.5 $\mu$m. The deposition of the protective bilayer can be carried out within the FIB system.

Figure 2B:
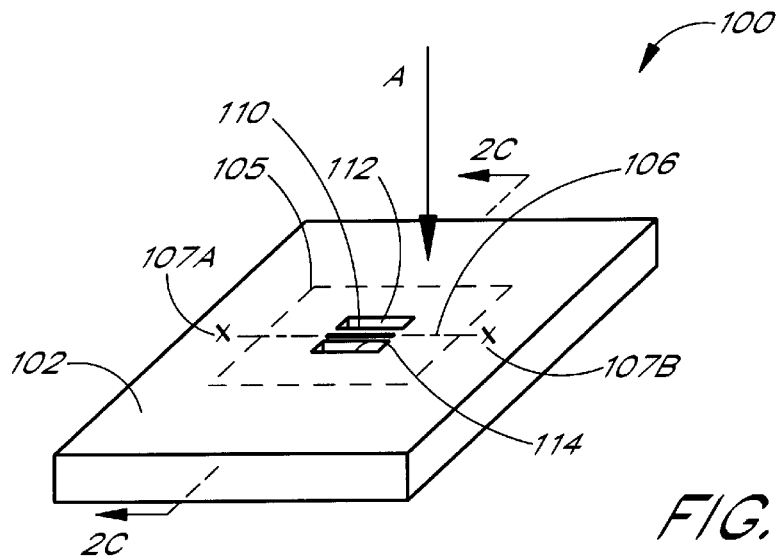
FIG. 2B is a perspective view of the substrate shown in FIG. 1 wherein a first electron transparent segment is formed using a focused ion beam technique.
Figure 2C:
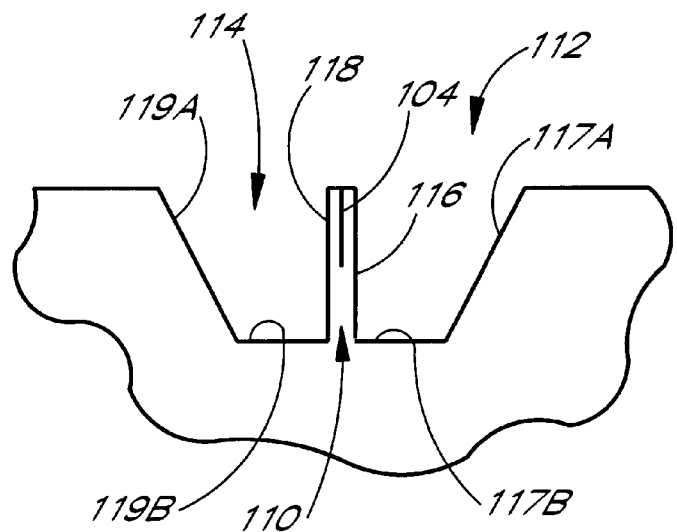
FIG. 2C is a partial cross-sectional view of the substrate taken along lines 2C—2C of FIG. 2B.

As illustrated in FIGS. 2B and 2C, using a focused ion beam (as indicated by arrow A), a first electron transparent segment 110 is formed by forming a first trench 112 and a second trench 114 on either side of the feature 104. The first electron transparent segment 110 preferably comprises a thin membrane having a first surface 116 and a second surface 118. Preferably, the surfaces 116 and 118 of the first segment 110 extend parallel to the Z-axis. It will be understood that, in other arrangements, the first electron transparent segment can have been previously formed, such as the emitter tip for a flat panel display.

Referring to FIG. 2C, the first trench 112 is defined by a first trench side wall 117A, a first trench floor 117B and the first surface 116 of the membrane 110. Similarly, the second trench 114 is defined by a second trench side wall 119A, a second trench floor 119B and the second surface 118 of the membrane 110. It will be understood that each of the trenches 112, 114 are further defined by end walls (not shown), roughly in xz plane, although these walls can also be sloped. Trenches 112 and 114 are preferably identical in size and shape, as shown in FIG. 2C.

As also shown in FIG. 2C, the first and second trench side walls 117A and 119A are preferably sloped, terminating at the first and second trench floors 117B and 119B. In this configuration, the inclination of each of the side walls 117A and 119A is preferably in the range of approximately 40°–50°, more preferably about 45°. The membrane may be milled, using a focused ion beam, into a rectangle having approximately 0.05–0.2 $\mu$m thickness, 10–20 $\mu$m width and 4–8 $\mu$m height (i.e., trench depth). In the illustrated embodiment, the membrane is sized to have 0.1 $\mu$m thickness, 15 $\mu$m width (along the y-axis) and 5 $\mu$m height. The first and second trench floors 112 and 114 are preferably formed with about a 2–6 $\mu$m length and 10–20 $\mu$m width, more preferably 3 $\mu$m length (in the x-direction) and 15 $\mu$m width (in the y-direction).

As is well known in the art of TEM specimen preparation, the FIB technique can be performed in a variety of ways. For example, in the preferred embodiment, the milling is carried out so that the feature 104 to be observed is preserved within the two parallel surfaces 116 and 118 of the membrane 110 while the membrane 110 is thinned down to final electron transparency. During the FIB process, the die 100 can be accurately milled by frequently observing the position of the cross-section reference line 106 through the imaging system of the FIB system, and then aligning the focused ion beam so as to avoid irradiation of the focused ion beam onto the reference line 106.

In an exemplary staged milling process, milling is initiated with a relatively high intensity focused ion beam and at a point that is about 6–12 $\mu$m away from the cross-section reference line 106. It will be understood that the relative intensity of the focused ion beam can vary with the ion beam current. Accordingly, higher ion beam current values provides higher intensity ion beams which are capable of removing more material in a shorter time period. In this initial stage, a preferred ion beam current is in the range of about 2,500–3,000 pico amperes, more preferably about 2,700 pico amperes. As the focused ion beam is moved closer to the cross-section reference line 106 and, hence, closer to the preferred membrane thickness of about 0.1 $\mu$m, the beam current is gradually reduced to about 350 pico amperes or lower, preferably about 70 pico amperes for the final polishing.

As noted above, throughout the FIB process, the milling of the membrane 110 is periodically checked in-situ by the imaging system of the FIB equipment. As is known in the art of FIB milling, the imaging system can include a secondary electron imaging system using secondary electrons which are generated as a result of interactions between the ions of the focused ion beam and the atoms of the material of the die 100. The FIB process can be accomplished using standard focused ion beam equipment such as that sold under the trade name FEI 200 FIB, available from the FEI Co. of Hillsboro, Oreg. Once the membrane 110 is formed, the die 100 is taken out of the FIB equipment and removed from the specimen holder.

Figure 2D:
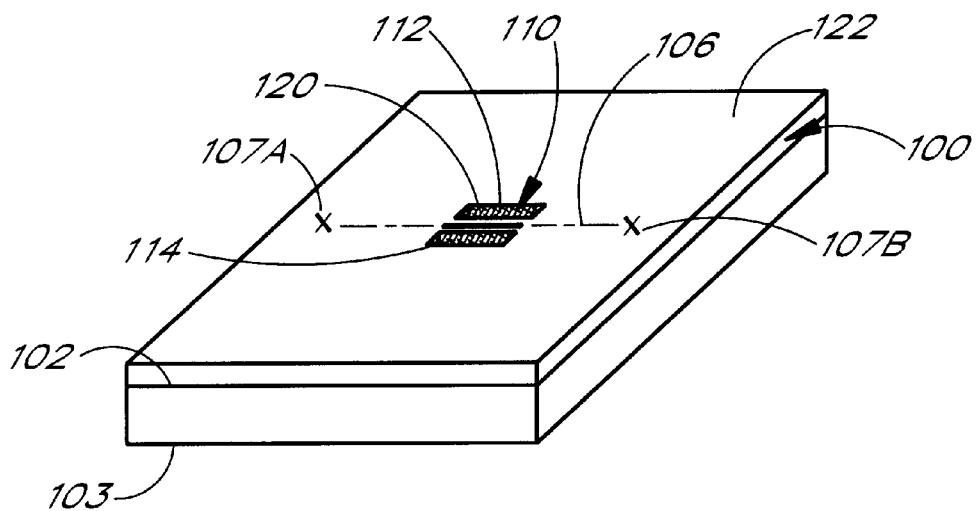
FIG. 2D is a perspective view of the substrate shown in FIG. 2B, wherein a glass layer is adhered on top of the substrate.

As illustrated in FIG. 2D, following the formation of the first electron transparent segment 110 (i.e., membrane), the trenches 112 and 114 are filled with a filler 120 and a layer of protective material 122 is subsequently attached to the die 100. The protective layer 122 is preferably transparent, to permit identification of the first segment 110 during the following procedures. In the illustrated embodiment, the layer of protective material 122 comprises a thin glass layer. As will be explained herein below, the protective layer 122 protects the membrane 110 during subsequent processing steps. The filler 120 preferably comprises a removable adhesive, such as SUPER GLUE™, which is readily dissolvable in acetone. As will be described more fully below, the filler 120 fills the trenches 112 and 114 and thereby supports the fragile membrane 110 throughout the remainder of the preparation process.

After gluing the protective layer 122 on the upper surface 102 of the die 100, a second electron transparent segment is preferably formed using a second material thinning technique. The second material thinning technique preferably comprises a wedge-forming technique (or "wedge technique" for short), most preferably utilizing a polishing process. The thinning process reduces the size of the die 100 along the x-axis of the die 100. As will be described more fully below, the size reduction preferably progresses along the x-axis toward the cross-section reference line 106.

Figure 3A:
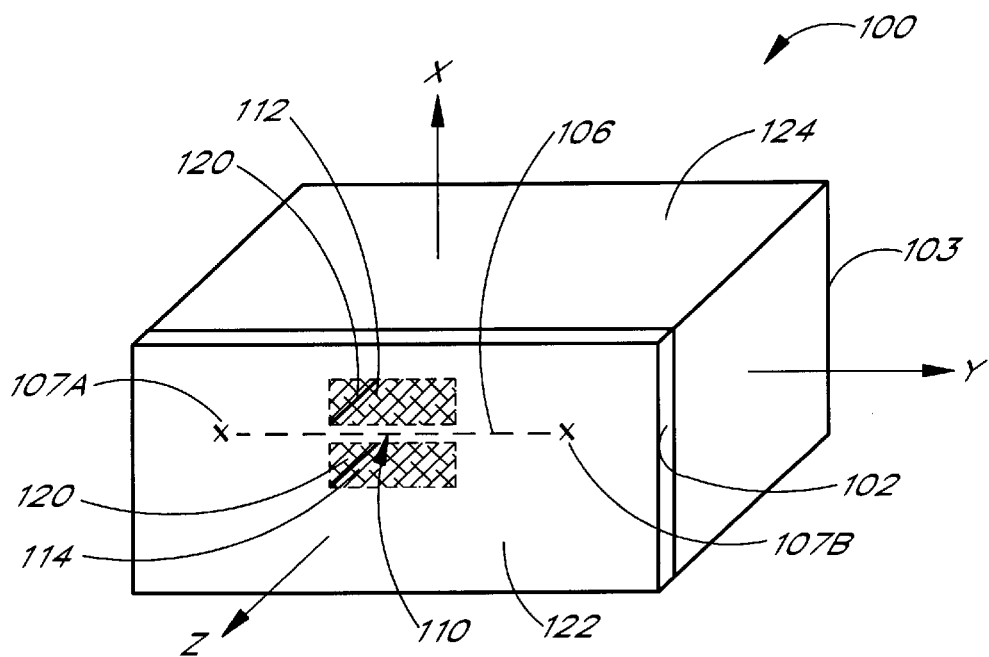
FIG. 3A is a perspective view of the substrate shown in FIG. 2D, wherein a first specimen surface is prepared for polishing.

As illustrated in FIG. 3A, the substrate 110 of FIG. 2D is rotated 90° so that the top surface 102 (covered by protective layer 122) faces forward and the x-axis is vertical. Size reduction along the x-axis is then initiated by defining a first specimen surface 124 of the die 100. The first specimen surface 124 is preferably configured to be parallel to the cross section reference line 106 and the membrane 110 of the die 100. The first specimen surface 124 may be formed by cutting the die 100 parallel to a yz plane and adjacent to first trench 112 as in the manner shown in FIG. 3A. The cutting process of the die 100 is preferably carried out using a wire saw or a thin diamond impregnated wheel. After the cutting process, the distance between the first surface 116 of the membrane 110 and the resulting first specimen surface 124 is preferably in the range of about 0.3–1.0 mm, more preferably about 0.5 mm. It will be appreciated from the following description that this initial cut reduces the process time on the following polishing process.

Figure 3B:
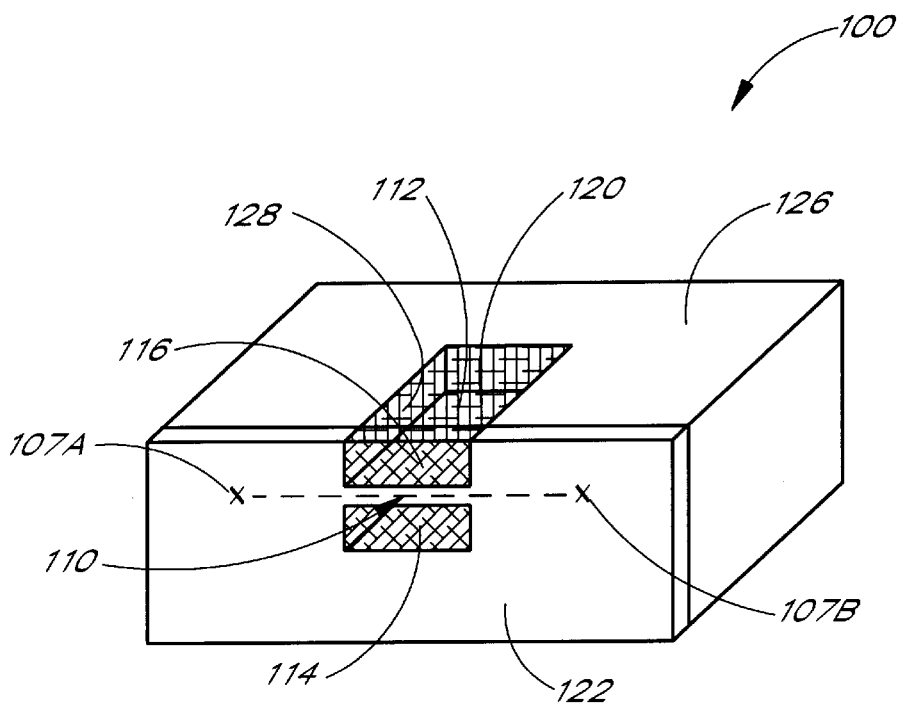
FIG. 3B is a perspective view of the substrate shown in FIG. 3A, after a polishing step.

As illustrated in FIG. 3B, after forming the first specimen surface 124, a portion of the die 100 and the filler layer 120 is removed from the first specimen surface 124. The removal at least partially reduces the die thickness to a desirable specimen thickness. In the illustrated embodiment, this also removes adjacent sheltering walls of the substrate to expose the first or upper surface 116 of the first segment 110.

Removal is preferably by uniformly polishing to form a first finished specimen surface 126. In order to form the first finished specimen surface 126, the first specimen surface 124 is polished along the x-axis and towards the membrane 110 until at least a portion of first trench side wall 117A, and preferably a portion of the first floor 117B of the first trench 112, (see FIG. 2C) is removed. For the purpose of clarity, any remaining portions of the first trench side wall 117A and remaining portions of the first trench floor 117B and the first trench end walls will be referred to as remaining first side walls 128 of the membrane 110 hereafter. The first finished specimen surface 126 is preferably flat and substantially parallel to the membrane 110, while the remaining first side walls 128 are substantially parallel to the x-axis and of approximately uniform height.

During the polishing process, the membrane 110 is protected by the glass protective layer 122 and the filler 120 filling the trench 112. When the polishing process is completed, the vertical distance between the first surface 116 of the membrane 110 and the first finished specimen surface 126 (i.e., the height of the remaining first side walls 128) is in the range of approximately 0.5–2.0 $\mu$m, preferably less than about 1 $\mu$m.

The preferred polishing process of the wedge technique comprises a mechanical polishing process, advantageously utilizing a tripod polisher device and an abrasive medium. The abrasive medium preferably comprises a series of diamond polishing films.

Diamond films are used to ensure a smooth finish on specimen surfaces and are well-known in the art of TEM specimen preparation. Diamond films are generally used on glass polishing wheels. As a rule of thumb, as the advancing plane of diamond polishing film approaches the membrane 110, diamond film particle size (or grit size) is gradually made finer to slow down material removal and to ensure a smooth finish on the first finished surface 126. An exemplary diamond film polishing sequence may be as follows. The polishing process is initiated with 15 $\mu$m grit size when the first specimen surface 124 (FIG. 3A) is about 300–400 $\mu$m away from the first or upper surface 116 of the membrane 110. As the distance between the upper surface 116 of the membrane 110 and the first specimen surface 124 is decreased in stages to about 100–150 $\mu$m, 50–70 $\mu$m, 20–30

μm and 7–10 μm, the grit size of the diamond films is correspondingly reduced to 6 μm, 3 μm, 1 μm and 0.5 μm, respectively. Such diamond polishing films are available from 3M Corporation, St Paul, Minn. The tripod polisher device is commercially available from South Bay Technology Inc.

Figure 3C:
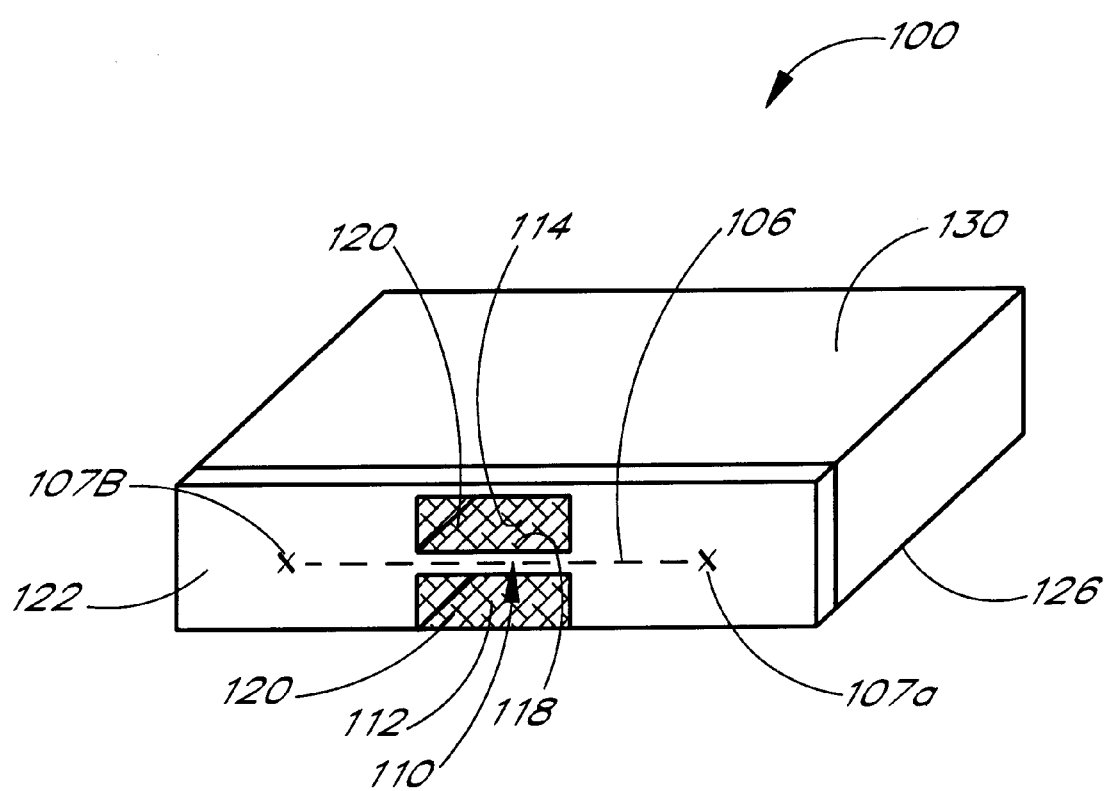
FIG. 3C is a perspective view of the substrate shown in FIG. 3B, wherein a second specimen surface is prepared for polishing.

As shown in FIG. 3C, once the first finished specimen surface 126 is formed, the die 100 is flipped and a second specimen surface 130 is defined. Definition of the second specimen surface is accomplished by removing portions of the die 100 and the filler layer 120, to reduce the substrate to a desired specimen thickness. In the illustrated embodiment, this also removes adjacent sheltering walls of the substrate to expose the second surface 118 of the first segment 110.

This removal is preferably performed by initially cutting the die 100 with the same process sequence which was used for forming the first specimen surface 124 (see FIG. 3B) as described above. As in the case of forming the first specimen surface 124, an initial cut to form the second specimen surface 130 reduces the process time of the following tripod polishing. The second specimen surface 130 defined by the initial cut can be formed adjacent to the second trench 114. In the illustrated embodiment, the second specimen surface 130 is thus parallel to the first finished specimen surface 126. The thickness of the die 100 along the x-axis is preferably in the range of approximately 0.4–0.6 mm, more preferably about 0.5 mm.

Figure 4A:
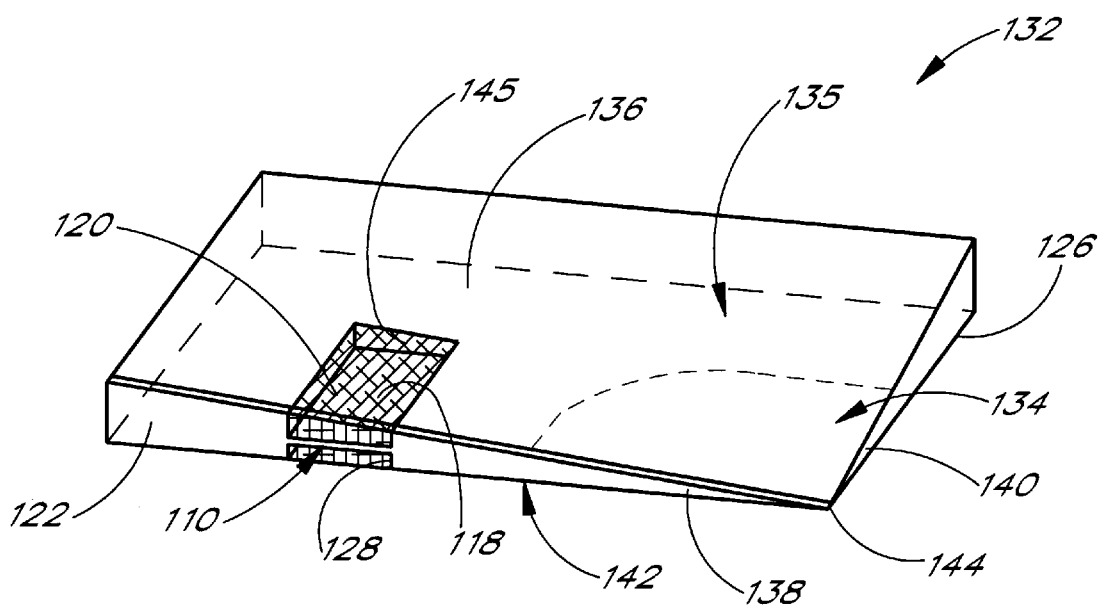
FIG. 4A is a perspective view of a cross-sectional TEM specimen having a second electron transparent segment.

As illustrated in FIG. 4A, after forming the second specimen surface 130, a cross-sectional TEM specimen 132 is defined by forming a second electron transparent segment 134 (dotted region). The second electron transparent segment 134 may be formed by removing the second specimen surface 130 (FIG. 3C) at an angle relative to the first finished specimen surface 126, thereby forming a second finished specimen surface 136. More preferably, the second electron transparent segment 134 has a double wedge structure having a first wedge 138 tapered along the y-axis and a second wedge 140 tapered along the z-axis.

Preferably, the double wedge structure is created by slightly tilting the die 100 (FIG. 3C) towards a front edge 142 and a corner 144 of the TEM specimen as the die 100 is being polished. A front edge 142, originally the upper surface 102 of the die 100 (FIG. 1), includes a surface of the membrane 110 and the glass protective layer 122 adjacent to the membrane 110. Preferably, the TEM specimen 132 is polished until the apexes of the first wedge 138 and the second wedge 140 meet at the corner 144. For the preferred dimensions, the tilt angle is in the range of about 0.1°–1, more preferably less than about 0.5°.

Additionally, as the second finished surface 136 is formed, at least a portion of the second trench side wall 119A is removed. Preferably, all of the side wall 119A is removed and portions of the second trench floor 119B and the second trench end walls of the second trench 114 are also removed. For the purpose of clarity, any remaining portions of the second trench side wall 119A and remaining portions of the second trench floor 119B and second trench end walls will be referred to as the remaining second side walls 145 of the second trench 114. As the polishing process advances toward definition of the second finished surface 136, the thickness of the double wedge structure, the height of the remaining second trench side walls 145, and the thickness of the second electron transparent segment 134 is progressively reduced. It will be understood that the remaining second side walls 145 are not of uniform height. Accordingly, because of the tilting angle, as the height of the remaining second trench side walls 145 is reduced down to about 0.5–1.0 μm, the thickness (in the x-axis) of the segment 134 becomes less than about 0.1 μm, which is in the electron transparency range for a TEM specimen.

The distance between the border of the second electron transparent segment 134 and the membrane 110 is preferably about 200–400 μm, more preferably 300 μm. The preferred second electron transparent segment 134 has a length of about 500–800 μm (along the first wedge 138), and a width of about 5–10 μm (along the second wedge 140).

Having exposed both sides of the membrane 110 by thinning the surrounding substrate, the glass protective layer 122 and the filler 120 in the trenches 112 and 114 are then removed from the specimen 132, preferably by dissolving the filler 120 (also serving as the adhesive) in acetone or other applicable solvent. The filler 120 and the protective layer 122 have thus protected the thin membrane 110 during the cutting, grinding and polishing steps which expose the membrane 110. In other arrangements, the filler can also fill the area around an emitter tip and a protective layer (preferably transparent) adhered to the surface transverse to the axis of removal on either side of the emitter.

Figure 4B:
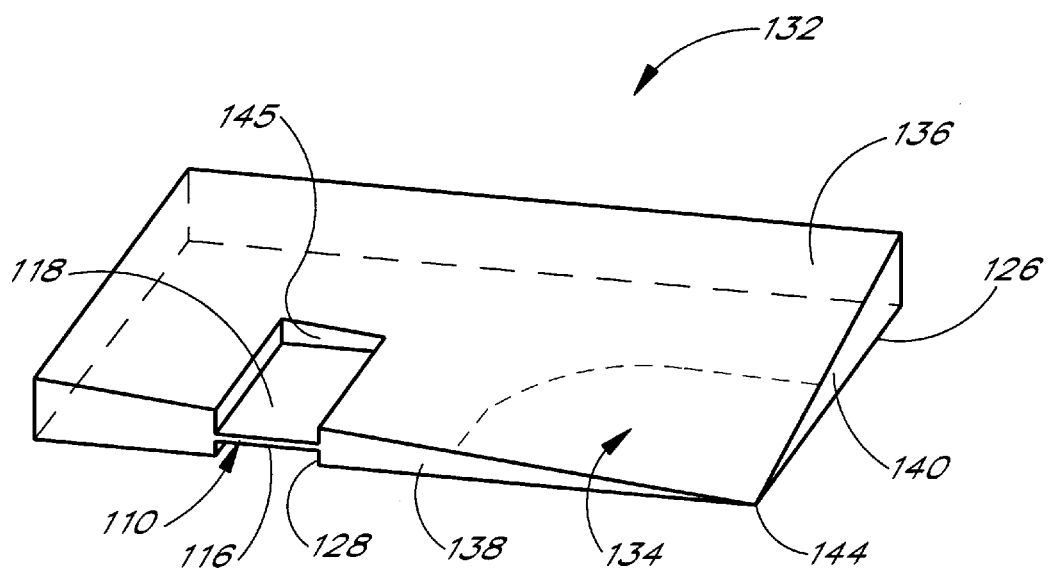
FIG. 4B is a perspective view of the cross-sectional transmission electron microscope specimen of the present invention.

FIG. 4B shows the cross-sectional TEM specimen 132 constructed in accordance with the preferred embodiment. As shown in FIG. 4B, the TEM specimen 132 advantageously has a first electron transparent segment 110, as well as a larger second electron transparent segment 134. As previously explained, these two electron transparent segments 110 and 134 allow the cross sectional TEM examination of two separate locations on the TEM specimen 132. In particular, a specific feature in the membrane 110 can simultaneously be studied in comparison with the larger wedge structure having second electron transparent segment 134. Advantageously, EDS (Energy Dispersive X-ray) analysis can be performed on either of the segments. Since the height of the side walls is preferably less than about 0.5 μm, remaining side walls 128, 145 of the recesses in which membrane 110 is formed do not block X-rays during the EDS analysis of the membrane 110. In addition, if re-work is necessary, the TEM specimen 132 can be re-thinned using an ion mill process.

Although the foregoing invention has been described in terms of certain preferred embodiments, other embodiments will become apparent to those of ordinary skill in the art, in view of the disclosure herein. For example, steps of the preferred process can be performed in a sequence other than that described. Furthermore, one of skill in the art will readily appreciate the utility of certain of the disclosed steps, even in the absence of certain other of the disclosed steps. Accordingly, the present invention is not intended to be limited by the recitation of preferred embodiments, but is instead intended to be defined solely by reference to the appended claims.

We claim:

1. A cross-sectional electron microscope specimen, comprising:
   a first electron transparent segment of a substrate comprising a specific feature of interest; and
   a second electron transparent segment of said substrate, separate from said first segment comprising a representative bulk portion of said specimen.

2. The specimen of claim 1, wherein said first electron transparent segment comprises two substantially parallel surfaces separated by an electron transparent thickness.

3. The specimen of claim 2, wherein said first segment is formed by a focused ion beam process.

4. The specimen of claim 1, wherein said second electron transparent segment comprises a first surface and a second surface separated by a tapering thickness.

5. The specimen of claim 4, wherein said thickness tapers in two dimensions to form a double wedge structure.

6. The specimen of claim 5, wherein said double wedge structure is formed by polishing said first surface of said substrate at an angle with respect to said second surface.

7. The specimen of claim 1, wherein said second electron transparent segment is substantially larger than said first electron transparent segment.

8. A cross-sectional transmission electron microscope (TEM) specimen, comprising:
   a first electron transparent segment recessed by less than about 0.5 $\mu$m from a surface of a substrate die; and
   a second electron transparent segment having a tapered thickness.

9. The TEM specimen of claim 8, wherein said first electron transparent segment comprises an upper segment surface recessed relative to an upper die surface and a lower segment surface recessed relative to a lower die surface.

10. The TEM specimen of claim 8, wherein said second electron transparent segment comprises a portion of a double wedge structure.

11. A specimen for material analysis of an at least partially fabricated integrated circuit on a semiconductor substrate, the specimen having a first surface and a second surface, the specimen comprising:
   a first segment positioned within a trench formed in the specimen, the trench extending between the first and second surfaces, with the first segment oriented parallel to one of the first and second surfaces, the segment including a fabricated feature of the integrated circuit; and
   a second segment formed at a tapered edge of the specimen, the second segment including bulk material of the semiconductor substrate.

12. A process of preparing a transmission electron microscope (TEM) specimen, comprising:
   forming a first segment in the specimen, the first segment having a first upper surface and a first lower surface separated by a first electron transparent thickness; and
   removing an upper portion of the specimen after forming the first segment to expose the first upper surface.

13. The process of claim 12, further comprising removing a lower portion of the specimen after forming the first segment to expose the first lower surface.

14. The process of claim 13, wherein removing the upper and lower portions defines a second segment on the specimen, the second segment having a second upper surface and a second lower surface separated by a second electron transparent thickness.

15. The process of claim 14, wherein removing the upper and lower portions comprises forming a wedge.

16. The process of claim 15, wherein removing the upper and lower portions comprises forming a double wedge structure.

17. The process of claim 15, wherein forming the wedge comprises polishing the second upper surface and the second lower surface at an angle with respect to one another.

18. The process of claim 12, wherein forming the first segment comprises focused ion beam milling the specimen.

19. A method of forming a specimen of a substrate for material analysis in two distinct segments, the method comprising:
   milling a trench in a surface of the substrate on each side of a feature of interest to form an electron transparent membrane extending generally perpendicular to said surface;
   removing a first portion of the substrate to form a first finished specimen surface generally parallel to said membrane and expose a first surface of said membrane; and
   removing a second portion of the substrate to form a second finished specimen surface at an angle to said first finished specimen surface and expose a second surface of said membrane.

20. The method of claim 19, wherein said first and second surfaces of said membrane are parallel to one another.

21. The method of claim 19, wherein said first and second finished specimen surfaces define a specimen corner having an electron transparent thickness.

22. A method of preparing a specimen for cross-sectional analysis, the method comprising:
   focused ion beam milling a first trench on a first side of a feature of interest within a die;
   focused ion beam milling a second trench of a second side of the feature of interest to form a membrane;
   removing a first side wall of said first trench by polishing the die generally parallel to said membrane; and
   removing a second side wall of said second trench by polishing the die.

23. The method of claim 22, wherein removing the first side wall and removing the second side wall comprises polishing opposite surfaces of the die at different angles.

24. A process of preparing a transmission electron microscope (TEM) specimen, comprising:
   providing an electron transparent segment within a substrate;
   protecting the segment with a removable filler layer and a protective cover layer;
   removing portions of the substrate and the filler layer to reduce the substrate to a desired thickness; and
   removing the filler layer and the protective cover layer by dissolving the filler layer in solvent.

25. The process of claim 24, wherein the filler layer comprises an adhesive layer and the solvent comprises acetone.

26. The process of claim 24, further comprising mounting the specimen on a grid and analyzing the segment with a transmission electron microscope.

27. The process of claim 24, wherein the protective layer is transparent.

28. The process of claim 24, wherein providing the electron transparent segment comprises focused ion beam milling.

29. The process of claim 24, wherein providing the electron transparent segment comprises forming an emitter tip for a flat panel display.

30. The process of claim 24, wherein removing portions of the substrate and the filler layer comprises removing sheltering walls of the substrate adjacent the electron transparent segment to expose the electron transparent segment for transmission electron analysis.

* * * * *